US005593831A

United States Patent [19]

Shah et al.

[11] Patent Number: 5,593,831

[45] **Date of Patent: * Jan. 14, 1997**

[54] **NUCLEIC ACID PROBES FOR THE DETECTION OF *YERSINIA ENTEROLITICA***

[75] Inventors: Jyotsna S. Shah, Nashua, N.H.; Samuel W. Chan, Newton, Mass.; Theodore B. Pitman, Lynnfield, Mass.; David J. Lane, Milford, Mass.

[73] Assignee: Amoco Corporation, Chicago, Ill.

[ * ] Notice: The term of this patent shall not extend beyond the expiration date of Pat. No. 5,370,992.

[21] Appl. No.: 297,103

[22] Filed: Aug. 29, 1994

Related U.S. Application Data

[63] Continuation of Ser. No. 936,886, Aug. 27, 1992, Pat. No. 5,370,992, which is a continuation of Ser. No. 169,646, Mar. 18, 1988, abandoned.

[51] Int. Cl.$^{6}$ .......................... C07H 21/02; C07H 21/04; C12Q 1/68

[52] U.S. Cl. .......................... 435/6; 435/172.3; 435/810; 436/501; 536/23.1; 536/24.3; 536/24.32; 935/77; 935/78

[58] Field of Search .......................... 435/6, 172.3, 810; 436/501; 536/23.1, 24.1, 24.3–24.33; 935/77, 78

[56] References Cited

U.S. PATENT DOCUMENTS 5,370,992 12/1994 Shah et al. .................................. 435/6

*Primary Examiner*—Ardin H. Marschel
*Attorney, Agent, or Firm*—Norval B. Galloway

[57] ABSTRACT

Nucleic acid probes capable of specifically hybridizing to rRNA of *Yersinia enterocolitica* and not to rRNA of non-*Yersinia enterocolitica* are described along with methods utilizing such probes for the detection of *Yersinia enterocolitica* in food and other samples.

5 Claims, No Drawings

NUCLEIC ACID PROBES FOR THE DETECTION OF *YERSINIA ENTEROLITICA*

This application is a continuation of U.S. application Ser. No. 07/936,886, filed Aug. 27, 1992 (now U.S. Pat. No. 5,370,992); which is a continuation of U.S. application Ser. No. 07/169,646, filed Mar. 18, 1988 (now abandoned).

FIELD OF THE INVENTION

This invention relates to detecting bacteria belonging to the genus *Yersinia enterocolitica* and more specifically provides nucleic acid probes and compositions along with methods for their use for the specific detection of *Yersinia enterocolitica.*

BACKGROUND OF THE INVENTION

The term "*Yersinia enterocolitica*" as used herein, refers to the bacteria classified as such Bergey's Manual of Systematic Bacteriology (N. R. Krieg [ed.], 1984, 498–506, Williams & Wilkins). Detection of *Yersinia enterocolitica* (*Y. enterocolitica*) is important in various medical and public health contexts. *Yersinia enterocolitica* infection can cause a variety of symptoms ranging from those resembling a cold to gastroenterocolitis. Under-cooked or uncooked meats are frequently a source of human food-borne infection from these organsims but routine screening is both time consuming and difficult.

It is, therefore, an aspect of the present invention to provide a novel assay system capable of rapidly detecting *Yersinia enterocolitica* and which is generally applicable to environmental, food or clinical samples.

Pursuant to a standard laboratory method and method recommended by the F.D.A. (FDA/BAM Bacteriological Analytical Manual, Chapter 11, 6th Edition, 1984, Supplement 9/87', Association of Offical Analytical Chemist), the presence of *Yersinia enterocolitica* in environmental or dairy specimens (e.g., milk) has been traditionally detected by culturing an appropriately prepared sample on microbiological media under conditions favorable for growth of these organisms. The resulting colonies are then typically examined for morphological and biochemical characteristics, a process that generally is initiated 48 hours after acquisition of the sample and disadvantageously takes between 12–17 days to complete.

It is yet another aspect of the present invention to avoid the disadvantage associated with traditional culturing techniques and to employ nucleic acid probes to detect *Yersinia enterocolitica.*

It is yet another aspect of the present invention to provide probes which can hybridize to target regions which can be rendered accessible to the probes under normal assay conditions.

While Kohne et al. (1968) Biophyscial Journal 8:1104–1118 discuss one method for preparing probes to rRNA sequences they do not provide the teaching necessary to make *Yersinia enterocolitica* specific probes.

Pace and Campbell (1971) Journal of Bacteriology 107:543–547 discuss the homology of ribosomal ribonucleic acids from diverse bacterial species and a hybridization method for quantitating such homology levels. Similarly, Sogin, Sogin, and Moese (1972) Journal of Molecular Evolution 1:173–184 discuss the theoretical and practical aspects of using primary structural characterization of different ribosomal RNA molecules for evaluating phylogenetic relationships.

Fox, Pechman, and Moese (1977) International Journal of Systematic Bacteriology discuss the comparative cataloging of 16S ribosomal RNAs as an approach to prokaryotic systems. These references, however, fail to relieve the deficiency of Kohne's teaching with respect to *Yersinia enterocolitica.*

Ribosomes are of profound importance to all organisms because they serve as the only Known means of translating genetic information into cellular proteins, the main structural and catalytic elements of life. A clear manifestation of this importance is the observation that all cells have ribosomes.

Ribosomes contain three distinct RNA molecules which, at least in *E. coli,* are referred to as 5S, 16S, and 23S rRNAs. These names historically are related to the size of the RNA molecules, as determined by sedimentation rate. In actuality, however, they vary substantially in size between organisms. Nonetheless, 5S, 16S, and 23S rRNA are commonly used as generic names for the homologous RNA molecules in any bacteria, and this convention will be continued herein.

Hybridization is traditionally understood as the process by which, under predetermined reaction conditions, two partially or completely complementary single-stranded nucleic acids are allowed to come together in an antiparallel fashion to form a double-stranded nucleic acid with specific and stable hydrogen bonds. The stringency of a particular set of hybridization conditions is defined by the base composition of the probe/target duplex, as well as by the level and geometry of mispairing between the two nucleic acids. Stringency may also be governed by such reaction parameters as the concentration and type of ionic species present in the hybridization solution, the types and concentrations of denaturing agents present, and/or the temperature of hybridization. Generally, as hybridization conditions become more stringent, longer probes are preferred if stable hybrids are to be formed. As a corollary, the stringency of the conditions under which a hybridization is to take place (e.g., based on the type of assay to be performed) will largely dictate the preferred probes to be employed. Such relationships are well understood and can be readily manipulated by those skilled in the art. As a general matter dependent upon probe length, such persons understand stringent conditions to mean approximately 35° C.–65° C. in a salt solution of approximately 0.9 molar.

As used herein, probe(s) refer to synthetic or biologically produced nucleic acids (DNA or RNA) which, by design or selection, contain specific nucleotide sequences that allow them to hybridize under defined predetermined stringencies, specifically (i.e., preferentially) to target nucleic acid sequences.

A target nucleic acid sequence is one to which a particular probe capable of preferentially hybridizing.

Still other useful definitions are given as their first use arises in the following text. All references cited herein are fully incorporated by reference.

SUMMARY OF THE INVENTION

In accordance with the various principles and aspects of the present invention, there are provided nucleic acid probes and probe sets comprising DNA or RNA sequences which, under specific hybridization conditions, are capable of detecting the presence of ribosomal RNA (rRNA) molecules of *Yersinia enterocolitica* but which are not capable, under the same conditions, of detecting the rRNA of other related bacteria which may be present in the test sample.

The present invention also features an assay system for the utilization of these probes, the format of which can enhance the aforementioned desirable behavior of the probes. The assay system of the present invention advantageously exhibits the following enhanced performance capabilities with respect to other currently available means for detection of *Yersinia enterocolitica:* a) increased sensitivity; i.e., the ability to detect *Yersinia enterocolitica* in a given sample more frequently than currently available methods;

b) potentially significant reductions in assay cost due to the use of inexpensive reagents and reduced labor;

c) accurate identification of *Yersinia enterocolitica* even when the biochemically closely related species, Yersinia intermedia is present; and d) faster results because the test is performed on cultured cells which need not be grown further. Accordingly, the preferred test of this invention advantageously takes only two to four days to provide a result.

It has been discovered that other advantages incurred by directing the probes of the present invention against rRNA include the fact that the rRNAs detected constitute a significant component of cellular mass. Although estimates of cellular ribosome content vary, actively growing Yersinia bacteria may contain upwards of 5.0×10E+4 ribosomes per cell, and therefore 5.0×10E+4 copies of each of the rRNAs (present in a 1:1:1 stoichiometry in ribosomes). In contrast, other potential cellular target molecules such as genes or RNA transcripts thereof, are less ideal since they are present in much lower abundance.

A further unexpected advantage is that the rRNAs (and the genes encoding them) appear not to be subject to lateral transfer between contemporary organisms. Thus, the rRNA primary structure provides an organism-specific molecular target, rather than a gene-specific target as would likely be the case, for example of a plasmid-borne gene or product thereof which may be subject to lateral transmission between contemporary organisms.

Additionally, the present invention provides probes to *Yersinia enterocolitica* rRNA target sequences which are capable of distinguishing two distinct classes of *Yersinia enterocolitica.* A preferred mixture of two probes can hybridize to the target region in all such *Yersinia enterocolitica.* Advantageously, these same rRNA target sequences are sufficiently different in most non-*Yersinia enterocolitica* rRNAs that, under the preferred assay conditions of the present invention, the probe(s) of the present invention hybridize to *Yersinia enterocolitica* rRNAs and do not generally hybridize to non-*Yersinia enterocolitica* rRNAs. These probe characteristics are defined as inclusivity and exclusivity, respectively. The discovery that probes could be generated with the extraordinary inclusivity and exclusivity characteristics of those of the present invention with respect to *Yersinia enterocolitica* was unpredictable and unexpected.

In a particularly preferred embodiment of the invention, an assay method for detecting *Yersinia enterocolitica* is provided in which bacteria in the sample to be tested are preferably grown for a limited time under conditions which Foster rapid and abundant growth of any *Yersinia enterocolitica* in the sample and which are biased against the growth of many closely related bacteria. Hybridization analysis using the preferred probes of the present invention is then advantageously performed on the sample after this growth period.

Another preferred embodiment includes probes capable of distinguishing the closely related species of *Yersinia intermedia* from *Yersinia enterocolitica* without depending upon the cumbersome and time consuming traditional biochemical tests.

BRIEF DESCRIPTION OF THE TABLES

Further understanding of the principles and aspects of the present invention may be made by reference to the tables wherein:

Table 1 Shows alignment of the nucleotide sequences of the preferred probes of the present invention with the nucleotide target sequence including the "core" region from 455 to 477 of *Yersinia enterocolitica* 16S rRNA (using the *E. coli* position numbering convention) along with relevant portions of the 16S rRNAs from *Escherichia coli* (*E. coli*), *Proteus vulgaris* (*Pr. vulga*), *Yersinia enterocolitica* type strain ATCC 9610 (*Y. ent*9610), and *Yersinia enterocolitica* isolate RF 954 (*Y. ent*954). RNA sequences are written 5' to 3', probe sequences are DNA and written 3' to 5'. Lower case c in certain of the probes indicates a modified cytosine residue to which a reporter group may or may not be attached depending on the assay form employed. Probes of the 880 series (880, 1062) are shown, along with the "core" region of variation upon which they are based, below their "parent" sequence, *Y. ent*9610. The 926 series of probes (926, 1111, 1112, 1113, 1063) and the 926 "core" sequence are shown below their "parent" sequence, *Y. ent* 954. Probe 927 and the "core" variation upon which it is based are shown below its "parent sequence", *Y.inte*814. Probe 1071 is a detection probe which is designed to be used with any of the 880, 926 or 927 probes.

Table 2 Exemplifies the inclusivity behavior of the preferred probes toward a representative sampling of Yersinia strains.

Table 3 Exemplifies the exclusivity behavior of the preferred probes toward a representative sampling of non-Yersinia strains.

Table 4 Provides inclusivity data related to the preferred liquid hybrid testing format of Example 1.

Table 5 Provides exclusivity data related to the preferred liquid hybrid testing format of Example 1.

Table 6 Provides data showing detection of *Yersinia enterocolitica* in food samples with the preferred probes in a preferred format of the present invention.

DETAILED DESCRIPTION OF THE INVENTION AND BEST MODE

The first step taken in the development of the probes of the present invention involved identification of regions of 16S and/or 23S rRNA which could potentially serve as target sites for *Yersinia enterocolitica* specific nucleic acid probes. As a practical matter, it is difficult to predict, a priori, which non-*Yersinia enterocolitica* organisms might be present in any test sample. Because of the large number of such potential non-*Yersinia enterocolitica* bacteria, demonstrating exclusivity for any given probe sequence is not only unpredictable but also extremely difficult and laborious. A more rigorous criterion was adopted to obviate the need to know, during initial stages of research and development, what non-*Yersinia enterocolitica* bacteria might be present in all test samples that ultimately will be screened using the probe. This entailed knowledge of the phylogenetic relationships among Yersinia and between Yersinia and other groups of bacteria. Specifically, an operating but previously unproven hypothesis was adopted that the exclusivity criterion could be satisfied by determining that if a particular target region in *Yersinia enterocolitica* rRNA, sufficiently different from the homologous region in the rRNA of representative yet close evolutionary relatives of *Yersinia enterocolitica* , could be identified, then a probe to such a sequence could be used to distinguish between the *Yersinia enterocolitica* and the relatives by hybridization assay. Based on phylogenetic observations, it was then extrapolated that rRNA sequences of more distantly related organisms, even though their actual identity may not necessarily be known, should be predictably different in a particular region of sequence than the aforementioned close evolutionary relative of *Yersinia enterocolitica*. However, it cannot be predicted, a priori whether such regions exist or if they do, where within the rRNA such regions will be located.

As our first step in identifying regions of *Yersinia enterocolitica* rRNA which could potentially serve as useful target sites for nucleic acid hybridization probes, nearly complete nucleotide sequences of the 16S and 23S rRNAs from *Yersinia enterocolitica, Yersinia intermedia, Yersinia kristensenii, Yersinia pseudo-tuberculosis,* etc. were determined. These were arbitrarily selected as representative of the evolutionary breadth of genus Yersinia. The nucleotide sequences of various portions of the rRNAs were determined by standard laboratory protocols either by cloning (Maniatis et al., 1982 Molecular Cloning: A Laboratory Manual, Cold Spring Harbor Laboratory, New York, 545pp) and sequencing (Maxam & Gilbert, 1977, Proceedings of the National Academy of Science, USA 74:560–564; Sanger et al., 1977 Proceedings of the National Academy of Science, USA 74:5463–5467) the genes which specify the rRNAs, and/or by direct sequencing of the rRNAs themselves using reverse transcriptase (Lane et al., 1985, Proceedings of the National Academy of Science, USA 82:6955–6959).

The identified nucleotide sequences were compared to one another and to other available rRNA nucleotide sequences, in particular to those of closely related bacteria such as Morganella, Proteus, Salmonella, Escherichia, and Pasturella. The preferred region of sequence shown in Table 1 was identified as potentially exhibiting useful exclusivity characteristics with respect to these species.

Further experimental testing of each nucleic acid probe was conducted to rigorously demonstrate whether the desired characteristics discussed above could indeed be obtained, namely: 1) adequate exclusivity to all even closely related non-*Yersinia enterocolitica* organisms, 2) useful inclusivity patterns with respect to *Yersinia enterocolitica* strains, and 3) accessibility of the target regions under various assay conditions that might actually be employed. Because of the extremely large number of organisms potentially relevant to defining exclusivity (presently ca. 22 enteric genera, comprised of some 69 species and 29 unspeciated 'biogroups', Farmer et al., 1985) and inclusivity (on the order of 8 species and biogroups of Yersinia) characteristics of test probes, an iterative strategy was adopted to test and refine potential probes. The probes were conveniently synthesized by standard phosphoramidite (Caruthers. M. H. et al. [1983], in Gene Amplification and Analysis, eds. Papas, T. S., Rosenberg, M., Charikjian, J. G., Pub. Elsevier, N.Y., Vol. 3 pp.1–26) techniques on an Applied Biosystems instrument.

"Dot blot" analysis, in accordance with well known procedures, was employed to preliminarily test the inclusivity and exclusivity properties of these first generation probes. As is known, dot blot analysis generally involves immobilizing a nucleic acid or a population of nucleic acids on a filter such as nitrocellulose, nylon, or other derivatized membrane which can be readily obtained commercially, specifically for this purpose. Either DNA or RNA can be easily immobilized on such a filter and subsequently can be probed or tested for hybridization under any of a variety of nucleic acid hybridization conditions (i.e. stringencies) with nucleotide sequences or probes of interest. Under stringent conditions, probes whose nucleotide sequences have greater complementary to the target sequence will exhibit a higher level of hybridization than probes containing less complementarity. For the oligonucleotide probes described herein, (i.e., 30–36 nucleotides in length and of average base composition) hybridization to rRNA targets at 60° C., for 14–16 hours (in a hybridization solution containing 0.9M NaCl, 0.12M Tris-HCl, pH 7.8, 6 mM EDTA, 0.1M KPO4, 0.1% SDS, 0.1% pyrophosphate, 0.002% ficoll, 0.02% BSA, and 0.002% polyvinylpyrrolidine) followed by three, 15 minutes post-hybridization washes at 60° C. to remove unbound probes (in a solution containing 0.03M NaCl, 0.004M Tris-HCl, pH 7.8, 0.2 mM EDTA and 0.1% SDS), would be sufficiently stringent to produce the levels of specificity and sensitivity demonstrated in the tables and examples. Techniques are also available in which DNA or RNA present in crude (unpurified) cell lysates can be immobilized without having to first purify the nucleic acid in question (reverred to herein as cytodots, see for example Maniatis, T., Fritsch, E. F. and Sambrook, J. (1982) Molecular Cloning, a Laboratory Manual). This latter approach significantly decreases the amount of effort required to screen for particular nucleotide sequences which may be present in the nucleic acids of any particular organism and, moreover, is advantageously amenable to the mass screening of large numbers of organisms. It, therefore, is the method of choice for exclusivity and inclusivity screening of potential nucleic acid hybridization probes vs large numbers of organisms.

A list of non-Yersinia bacteria which exemplify the type of bacteria that may be present in potentially *Yersinia enterocolitica* containing samples is given in Table 3. Note that these also represent many of the genera most closely related to Yersinia. As discussed above, a probe which demonstrates good exclusivity characteristics to such a broad representation of bacteria can reasonably be predicted to behave similarly to a much broader list of more distantly related enteric organisms.

Several other considerations also affect optimal design characteristics of a probe sequence. The first is consideration of the geometry of the probe with respect to itself (i.e., intramolecular interactions). It has been discovered that potentially useful target region of 16S and 23S rRNAs most often are located in regions that exhibit a substantial possibility for self-complementarity. As a result, probes to these regions can also exhibit self-complementarity. Because potential interactions between the probe and target sequences are governed by the same types of parameters that govern the intramolecular annealing of the target or probe sequences to themselves, it is possible, particularly under solution hybridization conditions, that self-complementary probes can render themselves inaccessible for hybridization to their target sequences. Thus, one important aspect of the probe design is to minimize such self-complementarity. This necessitates making a compromise between maximum utilization of *Yersinia enterocolitica*-specific sequences and acceptable probe geometry.

A second consideration in probe design arises with respect to the inclusivity criterion. The preferred probe will be one which, while displaying appropriate exclusivity behavior, can also hybridize to the rRNA(s) of all desired *Yersinia enterocolitica* bacteria. Because the species *Yersinia enterocolitica* itself is comprised of bacteria which exhibit significant phenotypic and genotypic (including, as disclosed below, rRNA) diversity, the design of such an "ideal" probe is greatly complicated. In practice, rather than searching for a single "universal" *Yersinia enterocolitica* probe, a set of *Yersinia enterocolitica*-specific probes is more preferably sought, each of which exhibits appropriate exclusivity along with a useful level of inclusivity. In aggregate, a preferred set of probes should ideally detect most or all *Yersinia enterocolitica* and no non-*Yersinia enterocolitica* bacteria. In such a set, for example, one probe may detect all but one or a few important *Yersinia enterocolitica* strains, and another probe may hybridize only to those few *Yersinia enterocolitica* strains missed by the first probe. Thus, although the probes disclosed below are characterized on an individual basis with respect to inclusivity characteristics, it should be recognized that the concept of "sets" of specific probes as detailed above is preferably considered in determining the importance of individual probes and in constructing assay kits.

The final steps of probe design and analysis ideally comprise testing real (e.g., food/clinical/environmental) samples and then selecting suitable probes for a final probe set so that the desirable properties are optimized under real assay conditions.

Probes

The foregoing probe selection strategy yielded a number of probes useful for identifying *Yersinia enterocolitica* bacteria in samples. As outlined in the Brief Description, Table 1 gives the probe sequences, aligned upon their target sites in the rRNAs of representative *Yersinia enterocolitica* strains. The "core" regions of nucleotide sequence differences within the target sites of *Yersinia enterocolitica* rRNA and representative non-*Yersinia enterocolitica* rRNA, which are the basis of the desirable discriminatory behavior of the probes, are also shown.

Three series of probes were developed: the "880" series and the "926" series, named after the first probe developed in each series and *Yersinia enterocolitica*-specific, and the "927" probe which is *Yersinia intermedia* specific. The members of each series differ somewhat in length, base composition, and "geometry" with respect to positioning of *Yersinia enterocolitica*-specific nucleotides in the 16S rRNA target sequence. Under given defined hybridization conditions, one probe from each series (880 and 926) will perform optimally with respect to inclusivity and exclusivity behavior. Probes from both series are capable of hybridizing, with exceptional exclusivity, to *Yersinia enterocolitica* under appropriately selected hybridization conditions. While either probe of the 880 or 926 series of the present invention demonstrates acceptable inclusivity for a specific subset of *Yersinia enterocolitica*, the ideal probe composition comprises a mixture of two probes, one from each series, in order to detect all Yersinia enterocolitica in all known cases. The probes are ideally selected in accordance with the particular assay format selected and its associated stringency characteristics. Table 2 shows the hybridization behavior of the probes toward rRNA target from representative species of Yersinia. The 880 series of probes was based on the 16S rRNA sequences of the *Yersinia enterocolitica* type strain ATCC 9610 and, as can be seen in Table 2, hybridizes strongly to that strain in addition to a number of other *Yersinia enterocolitica* strains. The 926 series of probes was based on the 16S rRNA sequence of *Yersinia enterocolitica* strain RF 954 (isolated in house but equivalent to human isolate E641, [D. A. Schiemann, Montana State University, Bozeman, Mont. 59717]). As shown in Table 2, the 926 probes hybridize strongly to a subset of *Yersinia enterocolitica* quite distinct from those to which the 880 probes hybridize. No other species of Yersinia are detected by either of the probes except for two strains of *Yersinia Kristensenii*, which are detected by the 926 probes. This minor deviation is unimportant from a clinical perspective. Note also that both probes distinguish between *Yersinia enterocolitica* and the biochemically difficult to distinguish, *Yersinia intermedia*.

*Yersinia intermedia* can be specifically distinguished from *Yersinia enterocolitica* by the 927 probe shown in Table 1.

Table 3 shows the hybridization behavior of the probes versus "cyto blots" of various non-Yersinia bacteria. In this experiment the probes were radioactively labelled with Phosphorous-32 for detection and quantitation. Little or no cross-hybridization of the shorter probe versions of each probe series was observed under the hybridization conditions employed in this experiment. These conditions comprised hybridizing at 60° C. for 14–16 hours in the hybridization solution previously described. Only the longest, less preferred probe version of the 926 probe series began to show limited reaction with non-Yersinia shown and thus defines an upper limit of optional probe length for use with these hybridization stringents. The more preferable intermediate length probe versions demonstrated the desired pattern of reactivity at the given hybridization condition. It will be readily recognized, however, that as assay formats of higher stringency are employed, the use of longer versions of the probes become more desirable since their level of cross-reactivity will decline while their level of sensitivity (hybridization efficiency) remains high.

EXAMPLE 1—General

A Homopolymer Capture, Dual Probe, Liquid Hybridization Format

Cultures containing Yersinia and/or non-Yersinia bacteria are grown in appropriate broth, then the nucleic acids are released by any of a number of appropriate lysis agents (e.g., NaOH, Guanidine salts, detergent, enzymatic treatment, or some combination of the aforementioned). Hybridization is carried out with two different probes or probe sets at least one of which, but not necessarily both, must be specific for the organism to be detected. In this example, the *Yersinia enterocolitica* specific "capture" probes, 880 and 926, are enzymatically tailed with 20–200 deoxyadenosine (dA) residues at their 3' termini. and the reporter probe, 1071, is labeled either chemically or enzymatically with radioactive Phosphorous (P-32) or other small ligand (e.g., fluorescein of biotin) which is used to detect the capture target molecules.

Generally, following cultivation/enrichment, bacteria present in the test samples are transferred in small aliquots to test tubes. The bacteria are lysed, the capture and detection probes are added, and hybridization is allowed to proceed in an appropriate solution at an appropriate temperature such as those already described. The solution containing the target/probe complex then is brought into contact with a surface containing bound deoxythymidine (dT) homopolymer 15–3000 nucleotides in length, under conditions that will allow hybridization between the dA and dT. In this example, the dT is bound to a plastic "dipstick"

which is submerged in the target/probe solution. If *Yersinia enterocolitica* ribosomal RNA was present in the test sample the dA tailed. *Yersinia enterocolitica* -specific capture probes would have hybridized to the target rRNAsequences present and, in turn, would be captured onto the dipstick. Unhybridized nucleic acids and cellular debris are washed away, leaving the captured DNA-RNA complex attached to the surface via the dA-dT duplex. The reporter probe also is bound to the dipstick via the chain of interactions—Capture surface-dT: dA-Capture probe:Target:Reporter Probe—only if the correct target nucelic acid is present. The bound, ligand derivatized (e.g., fluoresceinated) reporter probe then is detected by the addition of a ligand binding-enzyme complex (e.g., anti-fluorescein:alkaline phosphatase, streptavidin:horse radish peroxidase, etc.). Following incubation under conditions permitting specific binding of the detection complex, washing to remove non-bound enzyme, addition of chromogenic substrate and subsequent color development (typically 20–30 minutes), and the optional addition of color-termination solution, the developed color is measured colorimetrically. This reading (typically in the range of 0.2–>2.0 O.D. units) is compared to the negative control levels, a threshold or cutoff value is established, and a determination of the "significance" of the experimental levels is made. Tables 4 and 5 show the results of one such experiment, using pure culture of various Yersinia (Table 4) and non-Yersinia (Table 5) bacteria.

EXAMPLE 1—Specific

For dairy or meat product samples, 25 g of the food sample was added to 225 ml of Yersinia enrichment broth (PSBB, peptone-sorbitol-bile-broth: containing Sodium phosphate [dibasic] 8.23 g, Sodium phosphate [mono-basic] 1.2 g, Bile salts #3 1.5 g, Sorbitol 5 g, Peptone 10 g, Distilled water 1 liter) in order to obtain primary enrichment for *Yersinia enterocolitica* in the sample. The mixture was homogenized using a blender or stomacher as appropriate for the particular sample type, and then incubated in a bottle for 20–28 hours, most preferably 24 hours, at between 20° C. and 35° C., most preferably at 35° C.

For environmental testing, a swab or other environmental sample was placed in a flask or bottle containing 25 ml (or larger volume if required) PSBB, and incubated for 20–28 hours, most preferably 24 hours, at between 20°–35° C., most preferably at 35° C.

Secondary enrichment for all sample types was then performed. The primary enrichment culture was removed from incubation and mixed well. 1 ml (or 10 ml) of the primary enrichment culture was transferred to a test tube or bottle containing 10 ml (or 100 ml) PSBB and incubated for 24+ or –4 hours at 20°–35° C., most preferably at 35° C.

0.45 ml of the cultured cells were treated with 0.05 ml lysis solution (NaOH, 1.25N) by incubation at room temperature (15°–30° C.) for 5 minutes The bacterial lysates were neutralized with the addition of 0.1 ml of neutralization buffer ($KPO_4$:$NaPO_4$(1:1), 4M). The nucleic acids released from each sample was detected by addition of 0.05 ml specific capture and detector probe sets (containing between 1.4–2.8 microgram/ml of preferred capture probe set 880/926 although other combinations from the 880/926 series of probes may be used; and, 2–4 microgram/ml of detector probe 1071). A set of capture dipsticks were placed into the test tubes containing the bacterial lysates and the specific probes sets. The contents were incubated in a 65° C. water bath for 60 minutes to enable hybridization of specific capture and reporter probes to target nucleic acids and the capture of these specific DNA/rRNA hybrids to the dipsticks.

After hybridization, the dipsticks were washed by dipping the dipsticks in a wash basin containing enough wash solution to cover the active part of the dipstick (50 mM Tris, pH 7.5, 150 mM NaCl, 2 mM EDTA, and 0.1% Tween 20) for 1 minute. This process was then repeated in fresh solution.

The washed dipsticks were removed from the wash basin, blotted dry with absorbent paper, placed into a set of test tubes containing 0.75 ml antibody-enzyme conjugates (anti-fluorescein-horse radish peroxidase diluted in wash buffer), and allowed to incubate at room temperature for 20 minutes.

After allowing the antigen-antibody reaction to occur, the dipsticks were removed from the test tubes, washed and blotted in the same manner as described in the preceding two paragraphs. The dipsticks were placed into a set of labelled test tubes containing substrate-chromogen mixtures and allowed to incubate at room temperature for 20–30 minutes. The dipsticks were then removed and the color development step terminated by the addition of 0.25 ml 4N sulfuric acids. The optical density of the samples was measured colorimetrically.

Generally, the average of three negative controls (prepared from a selected non-*Yersinia enterocolitica* bacterium) was obtained and a value equal to 2.5X the average O.D. of the three negative controls chosen as the cutoff value. Sample tubes with higher O.D. value were considered positive for *Yersinia enterocolitica*, those with lower O.D. values indicated the absence of *Yersinia enterocolitica*. Results are shown in Table 6.

While the description of the invention has been made with reference to detecting rRNA, it will be readily understood that the probes described herein and probes complementary to those described herein will also be useful to detect the genes (DNA) encoding the rRNA and accordingly, such probes are to be deemed equivalents to the described probes and encompassed within the spirit and scope of the present invention and the appended claims.

TABLE 1

| YERSINIA ENTEROCOLITICA CORE AND PROBE SEQUENCE INFORMATION | |
|---|---|
| Pos. # | 405 ↓ … 455 ↓ … 477 ↓ … 490 ↓ |
| *E. coli* | . . . UGUAUGAAGAAGGCCUUCGGGUUGUAAAGUACUUUCAGCGGGGAGGAAGGGAGUAAAGUUAAUACCUUUGCUCAUUGACGUUACCC . . . |
| *Pr. vulga* | . . . UGUAUGAAGAAGGCCUUAGGGUUGUAAAGUACUUUCAGCGGGGAGGAAGGUGAUAAAGUUAAUACCUUUGUCAAUUGACGUUACCC . . . |
| Probe1071 | CCTCCGGAAGCCCAACATTTCGTGAAAGTCGCTCCTCC-5' |
| *Y. ent*9610 | . . . UGUGUGAAGAAGGCCuu CGGGUUGUAAAGCACUUUCAGCGAGGAGGAAGGCCAAUAACUUAAUACGUUGUUGGAUUGACGUUACUC . . . |
| Core Var | CCAAUAACUUAAUACGUUGUUGG |
| Probe 880 | TCCGGTTATTGAATTATGCAACAACCTAAC-5' |
| Probe1062 | CCTTCCGGTTATTGAATTATGCAACAACCTAACTGC-5' |
| *Y.ent* 954 | . . . UGUGUGAAGAAGGCCUUCGGGUUGUAAAGCACUUUCAGCGAGGAGGAAGGCAUAAAGGUUAAUAACCUUUGUGAUUGACGUUACUC . . . |
| Core Var | CAUAAAGGUUAAUAACCUUUGUG |
| Probe. 926 | TCCGTATTTCCAATTATTGGAAACACTAAC-5' |
| Probe111 | TCCGTATTTCCAATTATTGGAAACACTAACT-5' |
| Probe1112 | TCCGTATTTCCAATTATTGGAAACACTAACTG-5' |
| Probe1113 | TCCGTATTTCCAATTATTGGAAACACTAACTGC-5' |
| Probe1063 | CCTTCCGTATTTCCAATTATTGGAAACACTAACTGC-5' |
| *Y.int*E814 | . . . UGUGUGAAGAAGGCCUUCGGGUUGUAAAGCACUUUCAGCGAGGAGGAAGGCAGUCGUGUUAAUAGCACGAUUGAUUGACGUUACUC . . . |
| Core Var | CAGUCGUGUUAAUAGCACGAUUG |
| Probe 927 | TCCGTCAGCACAATTATCGTGCTAACTAAC-5' |

TABLE 2

YERSINIA - INCLUSIVITY DOT BLOT DATA

| Genus. species | Strain | Source | 880 | 926 | 927 |
|---|---|---|---|---|---|
| *Y. enterocolitica*(c) | 9610 | (1) | ++++ | – | – |
| *Y. enterocolitica* | 27729 | (1) | ++++ | – | – |
| *Y. enterocolitica* | 27739 | (1) | ++++ | – | – |
| *Y. enterocolitica* | 3715 | (1) | ++++ | – | – |
| *Y. enterocolitica* | 29913 | (1) | ++++ | – | – |
| *Y. enterocolitica* | E663 | (2) | ++++ | – | – |
| *Y. enterocolitica* | Y111 | (4) | ++++ | – | – |
| *Y. enterocolitica* | TAMU54 | (3) | ++++ | – | – |
| *Y. enterocolitica* | EM096 | (2) | ++++ | – | – |
| *Y. enterocolitica* | EM098 | (2) | ++++ | – | – |
| *Y. enterocolitica* | EM099 | (2) | ++++ | – | – |
| *Y. enterocolitica* | EM104 | (2) | ++++ | – | – |
| *Y. enterocolitica* | EM105 | (2) | ++++ | – | – |
| *Y. enterocolitica* | EM106 | (2) | ++++ | – | – |
| *Y. enterocolitica* | EM107 | (2) | ++++ | – | – |
| *Y. enterocolitica* | EM118 | (2) | ++++ | – | – |
| *Y. enterocolitica* | E651 | (2) | ++++ | – | – |
| *Y. enterocolitica* | E701 | (2) | ++++ | – | – |
| *Y. enterocolitica* | E661 | (2) | ++++ | – | – |
| *Y. enterocolitica* | E750 | (2) | ++++ | – | – |
| *Y. enterocolitica* | E759 | (2) | ++++ | – | – |
| *Y. enterocolitica* | E879 | (2) | ++++ | – | – |
| *Y. enterocolitica* | E665 | (2) | ++++ | – | – |
| *Y. enterocolitica* | E880 | (2) | ++++ | – | – |
| *Y. enterocolitica* | E881 | (2) | – | ++++ | – |
| *Y. enterocolitica* | E829 | (2) | – | ++++ | – |
| *Y. enterocolitica* | E857 | (2) | – | ++++ | – |
| *Y. enterocolitica* | E675 | (2) | – | ++++ | – |
| *Y. enterocolitica* | E719 | (2) | – | ++++ | – |
| *Y. enterocolitica* | E739 | (2) | – | ++++ | – |
| *Y. enterocolitica* | E766 | (2) | – | ++++ | – |
| *Y. enterocolitica* | E770 | (2) | – | ++++ | – |
| *Y. enterocolitica* | E839 | (2) | – | ++++ | – |
| *Y. enterocolitica* | E849 | (2) | – | ++++ | – |
| *Y. enterocolitica* | EM117 | (2) | – | ++++ | – |
| UNKNOWN | EM127 | (2) | – | ++++ | – |
| *Y. enterocolitica* | EM130 | (2) | – | ++++ | – |
| *Y. enterocolitica* | E237 | (2) | – | ++++ | – |
| *Y. enterocolitica* | E641 | (2) | – | ++++ | – |
| *Y. enterocolitica* | E668 | (2) | – | ++++ | – |
| *Y. enterocolitica* | E694 | (2) | – | ++++ | – |
| *Y. enterocolitica* | E720 | (2) | – | ++++ | – |
| *Y. enterocolitica* | E761 | (2) | – | ++++ | – |
| UNKNOWN | EM128 | (2) | – | ++++ | – |
| *Y. enterocolitica* | E817 | (2) | – | ++++ | – |
| *Y. enterocolitica* | E831 | (2) | – | ++++ | – |
| *Y. enterocolitica* | E844 | (2) | – | ++++ | – |
| *Y. enterocolitica* | E657 | (2) | – | ++++ | – |
| *Y. enterocolitica* | EM095 | (2) | – | ++++ | – |
| *Y. enterocolitica* | EM097 | (2) | – | ++++ | – |
| *Y. enterocolitica* | EM100 | (2) | – | ++++ | – |
| *Y. enterocolitica* | EM101 | (2) | – | ++++ | – |
| *Y. enterocolitica* | EM102 | (2) | – | ++++ | – |
| *Y. enterocolitica* | EM103 | (2) | – | ++++ | – |
| *Y. enterocolitica* | E641 | (2) | – | ++++ | – |
| *Y. enterocolitica* | E663R | (4) | – | ++++ | – |
| *Y. enterocolitica* | EHB20 | (5) | – | ++++ | – |
| *Y. enterocolitica* | C1017 | (2) | – | ++++ | – |
| *Y. enterocolitica* | C1119 | (2) | – | ++++ | – |
| *Y. enterocolitica* | C985 | (2) | – | ++++ | – |
| *Y. enterocolitica* | C1007 | (2) | – | ++++ | – |
| *Y. enterocolitica* | TAMU61 | (3) | – | ++++ | – |
| *Y. enterocolitica* | RF953 | (4) | – | ++++ | – |
| *Y. enterocolitica* | RF954 | (4) | – | ++++ | – |
| *Y. kristensenii* | E866 | (2) | – | ++++ | – |
| *Y. kristensenii* | E763 | (2) | – | ++++ | – |
| *Y. kristensenii* | 29911 | (1) | – | – | – |
| *Y. kristensenii* | E812 | (2) | – | – | +++ |
| *Y. kristensenii* | 33638 | (1) | – | – | – |
| *Y. kristensenii* | E802 | (2) | – | – | ++++ |
| *Y. kristensenii* | E803 | (2) | – | – | + |
| *Y. kristensenii* | E709 | (2) | – | – | – |
| *Y. kristensenii* | E812 | (2) | – | – | ++ |
| *Y. kristensenii* | E816 | (2) | – | – | +++ |
| *Y. frederiksenii* | 33641 | (1) | – | – | – |

TABLE 2-continued

| YERSINIA - INCLUSIVITY DOT BLOT DATA | | | | | |
|---|---|---|---|---|---|
| Genus. species | Strain | Source | 880 | 926 | 927 |
| *Y. fredricksenii* | E806 | (2) | – | – | – |
| *Y. aldovae* | 35236 | (1) | – | – | ++ |
| *Y. ruckeri* | 29908 | (1) | – | – | – |
| *Y. ruckeri* | 29473 | (1) | – | – | – |
| *Y. intermedia* | E814 | (2) | – | – | ++++ |
| *Y. intermedia* | EHB27 | (5) | – | – | ++++ |
| *Y. intermedia* | EH813 | (5) | – | – | ++++ |
| *Y. intermedia* | E820 | (2) | – | – | ++++ |
| *Y. intermedia* | E822 | (2) | – | – | ++++ |
| *Y. intermedia* | E825 | (2) | – | – | +++ |
| *Y. intermedia* | 29909 | (1) | + | – | ++++ |
| *Y. pseudotuberculosis* | 29833 | (1) | – | – | – |
| *Y. pseudotuberculosis* | 29910 | (1) | – | – | – |
| Yersinia sp. | 29912 | (1) | – | – | – |

++++ = positive control level of hybridization,
+++ = strong hybridization,
++ = weak but readily detectable,
+ = barely detectable,
– = zero.
Source key:
(1)ATCC, (2)D.A. Schienmann (Montana State Univ., Bozeman Montana 59717). (3)CDC, (4)GTS, in-house isolate from food/clinical samples, (5)Catherine W. Dannelly (Univ. Vermont, Coll. of Agriculture, Burlington VT 05405)

TABLE 3

| YERSINIA EXCLUSIVITY DOT BLOT DATA | | | | | | | |
|---|---|---|---|---|---|---|---|
| Strain | Source | Genus. species | 880 | 1062 | 926 | 1063 | 927 |
| e23566 | (1) | *Sa. typhimurium* | – | – | – | – | – |
| N99 | (1) | *E. coli* | – | – | – | – | – |
| 111(lac+) | (1) | *E. coli* | – | +/– | – | – | – |
| 72(drk. pnk) | (1) | *E. coli* | – | – | – | – | – |
| 47-24(lac+) | (1) | *E. coli* | – | – | – | – | – |
| 49-24(lac–) | (1) | *E. coli* | – | – | – | – | – |
| ATCC13313 | (2) | *Sh. dysenteriae* | – | – | – | – | – |
| ATCC29903 | (2) | *Sh. flexneri* | – | – | – | – | – |
| ATCC8700 | (2) | *Sh. boydii* | – | – | – | – | – |
| ATCC29929 | (2) | *Sh. boydii* C13 | – | – | – | – | – |
| ATCC29928 | (2) | *Sh. boydii* C10 | – | – | – | – | – |
| ATCC29930 | (2) | *Sh. sonnei* | – | – | – | – | – |
| S118A | (3) | *C. freundii* | – | – | – | ++ | – |
| S103B | (3) | *C. freundii* | – | – | – | – | – |
| S135 | (3) | *C. freundii* | – | – | – | – | – |
| 621-64 | (5) | *C. freundii* | – | – | – | – | – |
| 460-01 | (5) | *C. freundii* | – | – | – | + | – |
| ATCC29935 | (2) | *C. freundii* | – | – | – | + | – |
| ATCC33128 | (2) | *C. freundii* | – | – | – | +/– | – |
| ATCC8090 | (2) | *C. freundii* | – | – | – | – | – |
| Fanning 1 | (4) | *C. freundii* | – | – | – | + | – |
| Fanning 2 | (4) | *C. freundii* | – | – | – | – | – |
| Fanning 3 | (4) | *C. freundii* | – | – | – | – | – |
| Fanning 4 | (4) | *C. freundii* | – | – | – | – | – |
| Fanning 5 | (4) | *C. freundii* | – | – | – | – | – |
| S122B | (3) | *C. diversus* | – | – | – | – | – |
| 3613-63 | (3) | *C. diversus* | – | – | – | – | – |
| ATCC22156 | (2) | *C. diversus* | – | – | – | – | – |
| 9020-77 | (5) | *C. amalonaticus* | – | – | – | – | – |
| ATCC25406 | (2) | *C. amalonaticus* | – | – | – | – | – |
| ATCC25405 | (2) | *C. amalonaticus* | – | – | – | – | – |
| S121B | (3) | *E. agglomerans* | – | – | – | +++ | – |
| PB | (1) | *E. agglomerans* | – | – | – | – | – |
| ATCC29917 | (2) | *E. agglomerans* | – | – | – | – | – |
| ATCC29918 | (2) | *E. agglomerans* | – | – | – | – | – |
| ATCC29919 | (2) | *E. agglomerans* | – | – | – | +/– | – |
| ATCC29920 | (2) | *E. agglomerans* | – | – | – | – | – |
| ATCC29921 | (2) | *E. agglomerans* | – | – | – | – | – |
| ATCC29922 | (2) | *E. agglomerans* | – | – | – | – | – |
| ATCC29923 | (2) | *E. agglomerans* | – | – | – | – | – |
| ATCC29904 | (2) | *E. agglomerans* | – | – | – | ++ | – |
| ATCC29915 | (2) | *E. agglomerans* | – | – | – | – | – |
| ATCC29916 | (2) | *E. agglomerans* | – | – | – | – | – |

TABLE 3-continued

YERSINIA EXCLUSIVITY DOT BLOT DATA

| Strain | Source | Genus. species | 880 | 1062 | 926 | 1063 | 927 |
|---|---|---|---|---|---|---|---|
| ATCC27998 | (2) | *E. agglomerans* biogrp3 | – | – | – | – | – |
| S134 | (3) | *E. cloacae* | – | – | – | – | – |
| S121A | (3) | *E. cloacae* | – | – | – | – | – |
| 57 | (1) | *E. cloacae* | – | – | – | – | – |
| 124(lt. pnk) | (1) | *E. cloacae* | – | – | – | – | – |
| 126(lac+) | (1) | *E. cloacae* | – | – | – | – | – |
| ATCC29941 | (2) | *E. cloacae* | – | – | – | – | – |
| ATCC13047 | (2) | *E. cloacae* | – | – | – | – | – |
| S123A | (3) | *E. aerogenes* | – | – | – | – | – |
| ATCC29940 | (2) | *E. aerogenes* | – | – | – | +++ | – |
| ATCC13048 | (2) | *E. aerogenes* | – | – | – | +++ | – |
| ATCC33110 | (2) | *E. intermedium* | – | – | – | +/– | – |
| ATCC33072 | (2) | *E. amnigenus* | – | – | – | – | – |
| 108(wheat) | (1) | *E. sakazakii* | – | – | – | – | – |
| ATCC29544 | (2) | *E. sakazakii* | – | – | – | – | – |
| wheat | (1) | E. sp. CDC19 | – | – | – | – | – |
| ATCC33028 | (2) | *E. gergoviae* | – | – | – | – | – |
| ATCC35317 | (2) | *E. taylorae* | – | – | – | – | – |
| 69(lt. pnk) | (1) | *K. pneumoniae* | – | – | – | ++ | – |
| 72(mauve) | (1) | *K. pneumoniae* | – | – | – | – | – |
| 101(drk. pnk) | (1) | *K. pneumoniae* | – | – | – | – | – |
| ATCC13883 | (2) | *K. pneumoniae* | – | – | – | – | – |
| ATCC29939 | (2) | *K. pneumoniae* | – | – | – | – | – |
| S121C | (3) | *K. "oxytoca"* | – | +/– | – | – | – |
| RF501B | (1) | *K. "oxytoca"* | – | – | – | – | – |
| ATCC13182 | (2) | *K. oxytoca* | – | – | – | – | – |
| ATCC33531 | (2) | *K. planticola* | – | – | – | ++ | – |
| ATCC33257 | (2) | *K. terrigena* | – | – | – | + | – |
| ATCC11296 | (2) | *K. ozaenae* | – | – | – | +/– | – |
| 134(black) | (1) | *P. mirabilis* | – | – | – | – | – |
| 117(lac–) | (1) | *P. mirabilis* | – | – | – | – | – |
| ATCC25933 | (2) | *P. mirabilis* | – | – | – | – | – |
| ATCC29906 | (2) | *P. mirabilis* | – | – | – | – | – |
| ATCC7002 | (2) | *P. mirabilis* | – | – | – | – | – |
| S1188 | (3) | *P. vulgaris* | – | – | – | – | – |
| S133 | (3) | *P. vulgaris* | – | – | – | – | – |
| RF969 | (1) | *H. alvei* | – | – | – | +++ | – |
| 132(lac–) | (1) | *H. alvei* | – | – | – | +++ | – |
| RF953 | (1) | *Y. enterocolitica* D255 | – | – | ++++ | ++++ | – |
| RF954 | (1) | *Y. enterocolitica* I625 | – | – | ++++ | ++++ | – |
| RF955 | (1) | *Pas. mutocida* | – | – | – | – | – |
| RF972 | (1) | *Ser. marcescens* | – | – | – | – | – |
| 83(mauve) | (1) | *Ser. odorifera* | – | – | – | ++ | – |
| 106(lac–) | (1) | Ser. sp. | – | – | – | – | – |
| S107 | (3) | Ps. Sp. | – | – | – | – | – |
| IG977 | (1) | *Sh. boydii* C10 | – | – | – | – | – |
| IG978 | (1) | *E. coli* sp. | – | – | – | – | – |
| IG981 | (1) | *E. coli* sp. | – | – | – | – | – |
| 47-24(lac–) | (1) | *M. morganii* | – | +/– | – | – | – |
| 134(lac–) | (1) | *M. morganii* | – | – | – | – | – |
| ATCC8071 | (2) | *A. putrefaciens* | – | – | – | – | – |
| ATCC9886 | (2) | *Prov. alcalifaciens* | – | – | – | – | – |
| ATCC27790 | (2) | *Prov. alcalifaciens* | – | – | – | – | – |
| ATCC33673 | (2) | *Prov. rustigianii* | – | – | – | – | – |
| ATCC29944 | (2) | *Prov. rustigianii* | – | – | – | – | – |
| ATCC29914 | (2) | *Prov. stuartii* | – | – | – | – | – |
| ATCC837 | (2) | Aeromonas Ia 837 | – | – | – | – | – |
| ATCC19418 | (2) | *Haemophilus influenzae* | – | – | – | – | – |
| RF787 | (1) | *S. luciania* | – | – | – | – | – |
| RF890 | (1) | *S. brookfield* | – | – | – | – | – |
| IG3246 | (5) | S. sp.(CDC2269 [V]) | – | – | – | – | – |
| IG3242 | (5) | S. sp.(CDC1925 [V]) | – | – | – | – | – |
| IG3243 | (5) | S. sp.(CDC2229 [VI]) | – | – | – | – | – |
| RF905 | (1) | *S. arizonae* | – | – | – | – | – |
| E814 | (1) | *Y. intermedia* | – | – | – | – | – |
| ATCC9610 | (2) | *Y. entercolitica* | ++++ | ++++ | – | – | – |

++++ = positive control level of hybridization,
+++ = Strong hybridization,
++ = weak but readily detectable
+ = barely detectable,
– = zero.
Source Key:
(1)GTS, in-house isolate, (2)ATCC, (3) Silliker Laboratories, Chicago, IL., (4) George Fanning, Walter Reed Army Hospital, Washington, DC, (5) Don Brenner, CDC, Atlanta, GA.

TABLE 4

YERSINIA PANEL (pb880, pb926 mix)

| Genus. species | Strain | Source | Example OD Mean | Individual Probes (Dot Blots) 880 | 926 |
|---|---|---|---|---|---|
| *Y. enterocolitica*(c) | 9610 | (1) | 2.2 | ++++ | – |
| *Y. enterocolitica* | 27729 | (1) | 2.21 | ++++ | – |
| *Y. enterocolitica* | 27739 | (1) | 2.16 | ++++ | – |
| *Y. enterocolitica* | 3715 | (1) | 2.12 | ++++ | – |
| *Y. enterocolitica* | 29913 | (1) | 1.8 | ++++ | – |
| *Y. enterocolitica* | E663 | (2) | 1.85 | ++++ | – |
| *Y. enterocolitica* | TAMU54 | (3) | 2.08 | ++++ | – |
| *Y. enterocolitica* | EM096 | (2) | 1.86 | ++++ | – |
| *Y. enterocolitica* | EM098 | (2) | 1.53 | ++++ | – |
| *Y. enterocolitica* | EM099 | (2) | 1.57 | ++++ | – |
| *Y. enterocolitica* | EM104 | (2) | 1.09 | ++++ | – |
| *Y. enterocolitica* | EM105 | (2) | 1.52 | ++++ | – |
| *Y. enterocolitica* | EM106 | (2) | 1.51 | ++++ | – |
| *Y. enterocolitica* | EM107 | (2) | 1.14 | ++++ | – |
| *Y. enterocolitica* | EM118 | (2) | 1.94 | ++++ | – |
| *Y. enterocolitica* | E651 | (2) | 0.53 | ++++ | – |
| *Y. enterocolitica* | E701 | (2) | 1.47 | ++++ | – |
| *Y. enterocolitica* | E661 | (2) | 1.94 | ++++ | – |
| *Y. enterocolitica* | E750 | (2) | 2.03 | ++++ | – |
| *Y. enterocolitica* | E759 | (2) | 2.13 | ++++ | – |
| *Y. enterocolitica* | E879 | (2) | 2.12 | ++++ | – |
| *Y. enterocolitica* | E665 | (2) | 2.19 | ++++ | – |
| *Y. enterocolitica* | E880 | (2) | 2.12 | ++++ | – |
| *Y. enterocolitica* | E881 | (2) | 1.95 | – | ++++ |
| *Y. enterocolitica* | E829 | (2) | 2.02 | – | ++++ |
| *Y. enterocolitica* | E857 | (2) | 2.0 | – | ++++ |
| *Y. enterocolitica* | E675 | (2) | 1.88 | – | ++++ |
| *Y. enterocolitica* | E719 | (2) | 1.87 | – | ++++ |
| *Y. enterocolitica* | E739 | (2) | 1.77 | – | ++++ |
| *Y. enterocolitica* | E766 | (2) | 2.04 | – | ++++ |
| *Y. enterocolitica* | E770 | (2) | 1.96 | – | ++++ |
| *Y. enterocolitica* | E839 | (2) | 1.86 | – | ++++ |
| *Y. enterocolitica* | E849 | (2) | 2.22 | – | ++++ |
| *Y. enterocolitica* | EM117 | (2) | 1.6 | – | ++++ |
| UNKNOWN | EM127 | (2) | 0.63 | – | ++++ |
| *Y. enterocolitica* | EM130 | (2) | 0.54 | – | ++++ |
| *Y. enterocolitica* | E237 | (2) | 1.01 | – | ++++ |
| *Y. enterocolitica* | E641 | (2) | 0.83 | – | ++++ |
| *Y. enterocolitica* | E668 | (2) | 0.72 | – | ++++ |
| *Y. enterocolitica* | E694 | (2) | 0.8 | – | ++++ |
| *Y. enterocolitica* | E720 | (2) | 1.28 | – | ++++ |
| *Y. enterocolitica* | E761 | (2) | 1.13 | – | ++++ |
| UNKNOWN | EM128 | (2) | 1.1 | – | ++++ |
| *Y. enterocolitica* | E817 | (2) | 0.91 | – | ++++ |
| *Y. enterocolitica* | E831 | (2) | 1.43 | – | ++++ |
| *Y. enterocolitica* | E844 | (2) | 1.63 | – | ++++ |
| *Y. enterocolitica* | E657 | (2) | 1.99 | – | ++++ |
| *Y. enterocolitica* | E853 | (2) | 2.03 | – | ++++ |
| *Y. enterocolitica* | EM095 | (2) | 1.02 | – | ++++ |
| *Y. enterocolitica* | EM097 | (2) | 1.5 | – | ++++ |
| *Y. enterocolitica* | EM100 | (2) | 1.35 | – | ++++ |
| *Y. enterocolitica* | EM101 | (2) | 1.75 | – | ++++ |
| *Y. enterocolitica* | EM102 | (2) | 0.88 | – | ++++ |
| *Y. enterocolitica* | EM103 | (2) | 0.95 | – | ++++ |
| *Y. enterocolitica* | E641 | (2) | 1.25 | – | ++++ |
| *Y. enterocolitica* | E663R | (4) | 2.0 | – | ++++ |
| *Y. enterocolitica* | EHB20 | (5) | 1.05 | – | ++++ |
| *Y. enterocolitica* | C1017 | (2) | 1.51 | – | ++++ |
| *Y. enterocolitica* | C1119 | (2) | 1.46 | – | ++++ |
| *Y. enterocolitica* | C985 | (2) | 1.51 | – | ++++ |
| *Y. enterocolitica* | C1007 | (2) | 1.96 | – | ++++ |
| *Y. enterocolitica* | TAMU61 | (3) | 2.07 | – | ++++ |
| *Y. enterocolitica* | RF953 | (4) | 1.95 | – | ++++ |
| *Y. enterocolitica* | RF954 | (4) | 1.88 | – | ++++ |
| *Y. enterocolitica* | 0255 | (6) | 1.78 | – | + |
| *Y. enterocolitica* | K740 | (6) | 1.93 | – | + |
| *Y. enterocolitica* | K741 | (6) | 2.02 | – | + |
| *Y. enterocolitica* | T1389 | (6) | 2.16 | – | ++++ |
| *Y. kristensenii* | E866 | (2) | 1.98 | – | ++++ |
| *Y. kristensenii* | E763 | (2) | 0.05 | – | ++++ |
| *Y. kristensenii* | 29911 | (1) | 0.02 | – | – |
| *Y. kristensenii* | E812 | (2) | 0.03 | – | – |

TABLE 4-continued

YERSINIA PANEL (pb880, pb926 mix)

| Genus. species | Strain | Source | Example OD Mean | Individual Probes (Dot Blots) 880 | 926 |
|---|---|---|---|---|---|
| *Y. kristensenii* | 33638 | (1) | 0.04 | – | – |
| *Y. kristensenii* | E802 | (2) | | – | – |
| *Y. kristensenii* | E803 | (2) | 0.03 | – | – |
| *Y. kritensenii* | E709 | (2) | 0.06 | – | – |
| *Y. kristensenii* | E812 | (2) | 0.08 | – | – |
| *Y. kristensenii* | E816 | (2) | 0.09 | – | – |
| *Y. frederiksenii* | 33641 | (1) | 0.03 | – | – |
| *Y. fredricksenii* | E806 | (2) | 0.05 | – | – |
| *Y. aldovae* | 35236 | (1) | 0.04 | – | – |
| *Y. ruckeri* | 29908 | (1) | 0.04 | – | – |
| *Y. ruckeri* | 29473 | (1) | 0.04 | – | – |
| *Y. intermedia* | E814 | (2) | 0.02 | – | – |
| *Y. intermedia* | EHB27 | (5) | 0.03 | – | – |
| *Y. intermedia* | EHB13 | (5) | 0.02 | – | – |
| *Y. intermedia* | E820 | (2) | 0.09 | – | – |
| *Y. intermedia* | E822 | (2) | 0.02 | – | – |
| *Y. intermedia* | E825 | (2) | 0.02 | – | – |
| *Y. intermedia* | 29909 | (1) | 0.04 | + | – |
| *Y. philomiragia* | 25015 | (1) | 0.05 | – | – |
| *Y. pseudotuberculosis* | 29833 | (1) | 0.02 | – | – |
| *Y. pseudotuberculosis* | 29910 | (1) | 0.03 | – | – |
| *Y. pseudotuberculosis* | 044 | (6) | 0.05 | – | – |
| Yersinia sp. | 29912 | (1) | 0.01 | – | – |

OD Mean = OD measured on a mixture of probes 880, 926 and 1071
++++ = positive control level of hybridization,
+++ = strong hybridization,
++ = weak but readily detectable,
+ = barely detectable,
– = zero.
Source key:
(1)ATCC, (2)D. A. Schienmann (Montana State Univ., Bozeman Montana 59717), (3)CDC, (4)GTS, in-house isolate from food/clinical samples, (5)Catherine W. Dannelly (Univ. Vermont, Coll. of Agriculture, Burlington VT 05405). (6)Worcester Memorial Hospital, Worcester, MA.

TABLE 5

EXCLUSIVITY PANEL (926, 880)

| GENUS, SPECIES | SOURCE | ATCC@ | ALTERNATE# | OD |
|---|---|---|---|---|
| *Acaligenes denitrificans* | (2) | 27062 | | 0.03 |
| *Acinetobacter calcoacetius* | (1) | | (soy)115 | 0.04 |
| *Acinetobacter calcoacetius* | (2) | 19606 | | 0.02 |
| *Acinebacter lowbbie* | (2) | 9957 | | 0.03 |
| *Aeromonas hydrophilia* | (2) | 7965 | | 0.03 |
| *Aeromonas sorbia* | (1) | | IG 837 | 0.03 |
| *Bacillus cereus* | (2) | 14579 | | 0.03 |
| *Candida albicans* | (2) | 18804 | | 0.01 |
| *Candida glabrata* | (2) | 2001 | | 0.02 |
| *Citrobacter diversus* | (2) | 13048 | | 0.03 |
| *Citrobacter freundii* | (5) | | 3104-61 | 0.03 |
| *Citrobacter freundii* | (5) | | 1636-61 | 0.01 |
| *Citrobacter freundii* | (5) | | 2990-58 | 0.04 |
| *Citrobacter freundii* | (5) | | 3062-62 | 0.05 |
| *Citrobacter freundii* | (5) | | 1637-71 | 0.02 |
| *Citrobacter freundii* | (5) | | 6440-59 | 0.05 |
| *Citrobacter freundii* | (3) | | S135 | 0.03 |
| *Citrobacter freundii* | (3) | | S118A | 0.03 |
| *Citrobacter freundii* | (5) | | 2970-55 | 0.04 |
| *Citrobacter freundii* | (5) | | 892-61 | 0.03 |
| *Citrobacter freundii* | (5) | | 3158-63 | 0.02 |
| *Enterobacter auogenes* | (2) | 13048 | | 0.05 |
| *Enterobacter agglomerans* | (1) | | PB | 0.03 |
| *Enterobacter agglomerans* | (3) | | S121B | 0.03 |
| *Enterobacter cloacae* | (3) | | S134 | 0.03 |
| *Enterobacter cloacae* | (3) | | S121A | 0.02 |
| *Enterobacter cloacae* | (1) | | soy | 0.02 |
| *Enterobacter cloacae* | (1) | | IG 3068 | 0.02 |
| *Enterobacter cloacae* | (3) | | S103B | 0.04 |

TABLE 5-continued

EXCLUSIVITY PANEL (926, 880)

| GENUS, SPECIES | SOURCE | ATCC@ | ALTERNATE# | OD |
|---|---|---|---|---|
| *Enterobacter cloacae* | (1) | | 118 | 0.04 |
| *Enterobacter cloacae* | (1) | | 124(H pink) | 0.04 |
| *Enterobacter cloacae* | (1) | | 101 | 0.01 |
| *Enterobacter cloacae* | (1) | | 116 | 0.03 |
| *Enterobacter cloacae* | (1) | | 128 | 0.02 |
| *Enterobacter cloacae* | (1) | | 106 | 0.07 |
| *Enterobacter sakazakii* | (1) | | 108 | 0.05 |
| *Enterobacter sakazakii* | (1) | | 108(wheat) | 0.02 |
| *Enterobacter sakazakii* | (1) | | F-G1(soy) | 0.04 |
| *Enterobacter taylorae* | (2) | | 35317 | 0.03 |
| *Escherichia coli* | (7) | | D-cheese-1 | 0.03 |
| *Escherichia coli* | (1) | | N99 | 0.04 |
| *Escherichia coli* | (3) | | S-cheese-1 | 0.05 |
| *Escherichia coli* | (3) | | flour1 | 0.02 |
| *Escherichia coli* | (3) | | flour2 | 0.02 |
| *Escherichia coli* | (1) | | IG 898 | 0.03 |
| *Escherichia coli* | (1) | | YMC | 0.04 |
| *Escherichia coli* | (1) | | IG 833 | 0.02 |
| *Escherichia coli* | (1) | | IG 3012 | 0.02 |
| *Escherichia coli* | (3) | | 5-cheese-2 | 0.03 |
| *Escherichia coli* | (6) | | MGH 102641 | 0.04 |
| *Escherichia coli* | (6) | | MGH 102911 | 0.04 |
| *Escherichia coli* | (6) | | MGH 102075 | 0.05 |
| *Escherichia coli* | (6) | | MGH 102762 | 0.06 |
| *Escherichia coli* | (6) | | MGH 102005 | 0.04 |
| *Escherichia coli* | (6) | | MGH 103133 | 0.06 |
| *Escherichia coli* | (6) | | MGH 102565 | 0.04 |
| *Escherichia coli* | (6) | | MGH 103584 | 0.06 |
| *Escherichia coli* | (6) | | MGH 101544 | 0.07 |
| *Escherichia coli* | (6) | | MGH 102886 | 0.08 |
| *Escherichia coli* | (6) | | MGH 103580 | 0.06 |
| *Escherichia coli* | (6) | | MGH 103607 | 0.04 |
| *Escherichia coli* | (6) | | MGH 102705 | 0.09 |
| *Escherichia coli* | (6) | | MGH 102386 | 0.06 |
| *Escherichia coli* | (6) | | MGH 102520 | 0.07 |
| *Escherichia coli* | (1) | | D-H1(soy) | 0.06 |
| *Escherichia coli* | (6) | | MGH 102149 | 0.06 |
| *Escherichia coli* | (6) | | MGH 102979 | 0.03 |
| *Escherichia coli* | (6) | | MGH 103280 | 0.22 |
| *Escherichia coli* | (6) | | MGH 104114 | 0.05 |
| *Escherichia coli* | (6) | | MGH 103691 | 0.07 |
| *Escherichia coli* | (6) | | MGH 103253 | 0.08 |
| *Escherichia coli* | (6) | | MGH 102706 | 0.07 |
| *Escherichia coli* | (6) | | MGH 102718 | 0.07 |
| *Escherichia coli* | (6) | | MGH 102458 | 0.04 |
| *Escherichia coli* | (6) | | MGH 102525 | 0.07 |
| *Escherichia coli* | (6) | | MGH 103129 | 0.05 |
| *Escherichia coli* | (6) | | MGH 102901 | 0.05 |
| *Escherichia coli* | (6) | | MGH 102379 | 0.05 |
| *Escherichia coli* | (6) | | MGH 103666 | 0.03 |
| *Escherichia coli* | (6) | | MGH 103083 | 0.03 |
| *Escherichia coli* | (6) | | MGH 103765 | 0.03 |
| *Escherichia coli* | (6) | | MGH 103054 | 0.03 |
| *Escherichia coli* | (6) | | MGH 103327 | 0.05 |
| *Escherichia coli* | (6) | | MGH 102613 | 0.04 |
| *Escherichia coli* | (6) | | MGH 103834 | 0.03 |
| *Escherichia coli* | (6) | | MGH 103965 | 0.04 |
| *Escherichia coli* | (6) | | MGH 102121 | 0.03 |
| *Escherichia coli* | (6) | | MGH 10276 | 0.03 |
| *Escherichia coli* | (6) | | MGH 104007 | 0.2 |
| *Escherichia coli* | (6) | | MGH 102994 | 0.05 |
| *Escherichia coli* | (6) | | MGH 103603 | 0.03 |
| *Escherichia coli* | (6) | | MGH 102627 | 0.02 |
| *Escherichia coli* | (6) | | MGH 102687 | 0.04 |
| *Escherichia coli* | (6) | | MGH 102024 | 0.02 |
| *Escherichia coli* | (7) | | Cheese-2 | 0.02 |
| *Escherichia coli* | (6) | | MGH 103006 | 0.03 |
| *Escherichia coli* | (6) | | MGH 102109 | 0.03 |
| *Escherichia coli* | (6) | | MGH 103010 | 0.05 |
| *Klebsiella oxytoca* | (1) | | 112(soy) | 0.02 |
| *Klebsiella oxytoca* | (2) | 13182 | | 0.03 |
| *Klebsiella pneumoniae* | (3) | | S121C | 0.03 |
| *Klebsiella pneumoniae* | (1) | | IG3058 | 0.01 |

TABLE 5-continued

| GENUS, SPECIES | EXCLUSIVITY PANEL (926, 880) SOURCE | ATCC@ | ALTERNATE# | OD |
|---|---|---|---|---|
| | STRAIN | | | |
| *Klebsiella pneumoniae* | (1) | | 117(soy) | 0.01 |
| *Klebsiella pneumoniae* | (3) | | S122F | 0.02 |
| *Klebsiella pneumoniae* | (1) | | IG F-C5(soy) | 0.03 |
| *Listeria innocua* | (1) | | IG 3171 | 0.02 |
| *Listeria monocytogens* | (1) | | IG 3257 | 0.01 |
| *Listeria monocytogenes* | (1) | | IG 3168 | 0.03 |
| *Listeria seeligeri* | (1) | | IG 3381 | 0.02 |
| *Listeria seeligeri* | (1) | | IG 3352 | 0.02 |
| *Listeria welshimeri* | (1) | | IG 3289 | 0.02 |
| *Listeria welshimeri* | (1) | | IG 3298 | 0.03 |
| Micrococcus sp. | (1) | | IG03 | 0.02 |
| *Morganella morganii* | (1) | | IG 3063 | 0.03 |
| *Morganella morganii* | (2) | 25830 | | 0.02 |
| *Pasteurella gallinarum* | (2) | 13361 | | 0.04 |
| *Pasteurella multocida* | (2) | 19427 | | 0.03 |
| *Proteus mirabilis* | (1) | | IG 3098 | 0.02 |
| *Proteus myxofaciens* | (2) | 19692 | | 0.04 |
| *Proteus penneri* | (2) | 33519 | | 0.02 |
| *Proteus vulgaris* | (2) | 29905 | | 0.02 |
| *Proteus vulgaris* | (2) | 13315 | | 0.01 |
| *Provedencia stuartii* | (2) | 29914 | | 0.03 |
| *Providencia alcalifaciens* | (2) | 27930 | | 0.01 |
| *Providencia alcalifaciens* | (2) | 9886 | | 0.02 |
| *Providencia rettgerii* | (2) | 29944 | | 0.03 |
| *Providencia rustigianii* | (2) | 33673 | | 0.02 |
| *Pseudomonas acidovrans* | (2) | 15668 | | 0.03 |
| *Pseudomanas aerginosa* | (1) | | IG 928 | 0.02 |
| *Pseudomanas pickettii* | (2) | 13361 | | 0.02 |
| *Salmonella arizoniae* | (1) | | RF 913 | 0.02 |
| *Salmonella arizoniae* | (3) | | S942 | 0.02 |
| *Salmonella typhimurium* | (2) | 23566 | | 0.02 |
| *Salmonella weslaco* | (1) | | RF851 | 0.01 |
| *Staph aureus* | (1) | | IG F3 | 0.01 |
| *Staph aureus #50* | (2) | 12600 | | 0.14 |
| *Staph saprophyticus* | (2) | 15303 | | 0.02 |
| *Staph epidremidis* | (2) | | ID 62 | 0.02 |
| *Staph epidremidis* | (2) | | ID 63 | 0.01 |
| *Staph epidremidis* | (2) | 14990 | | 0.02 |
| *Strep agalactiae* | (2) | 13813 | | 0.02 |
| *Strep faecalis* | (2) | 19433 | | 0.03 |
| *Strep faecium* | (2) | 6056 | | 0.01 |
| *Strep mutans* | (2) | 25175 | | 0.02 |
| *Strep pneumoniae* | (2) | 6303 | | 0.04 |
| *Strep pyrogenes* | (2) | 19615 | | 0.04 |
| *Strep salivarus* | (2) | 13419 | | 0.02 |
| *Strep sanginis* | (2) | 10556 | | 0.01 |

Source key:
(1)ATCC, (2)D. A. Schienmann (Montana State Univ., Bozeman Montana 59717), (3)CDC, (4)GTS, in-house isolate from food/clinical samples, (5)Catherine W. Dannelly (Univ. Vermont, Coll. of Agriculture, Burlington VT 05405), (6)Massachusetts General Hospital, Boston, MA., (7)Deibel Laboratories, Madison, WI.

TABLE 6

NON-ISOTOPIC YERSINIA FOOD TRIAL #3

| # | Sample | Source | Species | Strain | cells/ sample | Primary Titer 48 H PSBB* | Secondary Titer 24 H GN* | Non-isotopic Hybridization Results 1° OD | 2° OD | 1° GT+ | 2° GT+ | Microbiological Confirmation |
|---|---|---|---|---|---|---|---|---|---|---|---|---|
| 1 | Cottage Cheese | (1) | *Y. enter* | 9610 | 1000 | | | 1.87 | 2.09 | + | + | + |
| 2 | Cottage Cheese | (1) | *Y. enter* | 9610 | 100 | | | 0.75 | 2.09 | + | + | + |
| 3 | Cottage Cheese | | control | | | | | 0.12 | 0.08 | − | − | − |
| 4 | Cottage Cheese | (3) | *Y. enter* | RF954 | 1310 | 1.5E+08 | 1.9E+08 | 2.07 | 2.09 | + | + | + |
| 5 | Cottage Cheese | (3) | *Y. enter* | RF954 | 131 | | | 1.91 | 2.09 | + | + | + |
| 6 | Cottage Cheese | | control | E663R | | | | 0.08 | 0.05 | − | − | − |
| 7 | Cottage Cheese | (3) | *Y. enter* | E663R | 1950 | 1.4E+08 | 6.4E+08 | 1.91 | 2.09 | + | + | − |
| 8 | Cottage Cheese | (3) | *Y. enter* | E663R | 195 | | | 2.04 | 2.08 | + | + | + |
| 9 | Cottage Cheese | | control | | | | | 0.15 | 0.05 | − | − | − |

TABLE 6-continued

NON-ISOTOPIC YERSINIA FOOD TRIAL #3

| # | Sample | Source | Species | Strain | cells/ sample | Primary Titer 48 H PSBB* | Secondary Titer 24 H GN* | Non-isotopic Hybridization Results 1° OD | 2° OD | 1° GT+ | 2° GT+ | Microbiological Confirmation |
|---|---|---|---|---|---|---|---|---|---|---|---|---|
| 10 | Cottage Cheese | (2) | *Y. enter* | E739 | 2480 | | | 1.65 | 2.07 | + | + | + |
| 11 | Cottage Cheese | (2) | *Y. enter* | E739 | 248 | | | 1.82 | 2.07 | + | + | + |
| 12 | Cottage Cheese | | control | | | | | 0.14 | 0.01 | – | – | – |
| 13 | Beef Franks | (1) | *Y. enter* | 9610 | 1000 | | | 0.35 | 0.84 | + | + | – |
| 14 | Beef Franks | (1) | *Y. enter* | 9610 | 100 | | | 0.15 | 0.09 | – | – | – |
| 15 | Beef Franks | | control | RF954 | | | | 0.11 | 0.06 | – | – | – |
| 16 | Beef Franks | (3) | *Y. enter* | RF954 | 1310 | 3.1E+08 | 6.4E+08 | 1.55 | 2.07 | + | + | – |
| 17 | Beef Franks | (3) | *Y. enter* | RF954 | 131 | | | 1.86 | 1.97 | + | + | – |
| 18 | Beef Franks | | control | | | | | 0.11 | 0.08 | – | – | – |
| 19 | Beef Franks | (3) | *Y. enter* | E663R | 1950 | 1.6E+08 | 1.1E+09 | 1.68 | 2.08 | + | + | – |
| 20 | Beef Franks | (3) | *Y. enter* | E663R | 195 | | | 1.02 | 1.58 | + | + | – |
| 21 | Beef Franks | | control | | | | | 0.10 | 0.05 | – | – | – |
| 22 | Beef Franks | (2) | *Y. enter* | E739 | 2480 | | | 0.41 | 1.88 | + | + | – |
| 23 | Beef Franks | (2) | *Y. enter* | E739 | 248 | | | 0.37 | 1.59 | + | + | + |
| 24 | Beef Franks | | control | | | | | 0.18 | 0.09 | – | – | – |
| 25 | Beef Franks w/det | (1) | *Y. enter* | 9610 | 1000 | | | 1.69 | 2.09 | + | + | + |
| 26 | Beef Franks w/det | (1) | *Y. enter* | 9610 | 100 | | | 0.49 | 0.45 | + | + | – |
| 27 | Beef Franks w/det | | control | | | | | 0.15 | 0.06 | – | – | – |
| 28 | Beef Franks w/det | (3) | *Y. enter* | RF954 | 1310 | 4.0E+08 | 4.1E+08 | 2.05 | 2.09 | + | + | + |
| 29 | Beef Franks w/det | (3) | *Y. enter* | RF954 | 131 | | | 1.58 | 2.08 | + | + | – |
| 30 | Beef Franks w/det | | control | | | | | 0.24 | 0.04 | – | – | – |
| 31 | Beef Franks w/det | (3) | *Y. enter* | E663R | 1950 | 3.0E+06 | 5.3E+08 | 1.06 | 2.07 | + | + | + |
| 32 | Beef Franks w/det | (3) | *Y. enter* | E663R | 195 | | | 0.36 | 2.07 | + | + | + |
| 33 | Beef Franks w/det | | control | | | | | 0.20 | 0.06 | – | – | – |
| 34 | Beef Franks w/det | (2) | *Y. enter* | E739 | 2480 | | | 0.91 | 1.70 | + | + | + |
| 35 | Beef Franks w/det | (2) | *Y. enter* | E739 | 248 | | | 2.01 | 2.00 | + | + | + |
| 36 | Beef Franks w/det | | control | | | | | 0.09 | 0.08 | – | – | – |

Positive cutoff: O.D. greater than 0.25, Negative (–): O.D. equal to or less than 0.25.
Control: No strain innoculated.
*Selective determination purely for informational purposed, not all cultures tested
Source key:
(1)ATCC, (2)D.A. Schienmann (Montana State Univ., Bozeman Montana 59717), (3)CDC, (4)GTS, in-house isolate from food/clinical samples, (5)Catherine W. Dannelly (Univ. Vermont, Coll. of Agriculture, Burlington VT 05405), (6)Massachusetts General Hospital, Boston, MA., (7)Deibel Laboratories, Madison, WI.

SUMMARY OF NON-ISOTOPIC YERSINIA FOOD TRIAL 3

File:data aj niy exp3

GT: 02/11/88
GT: Ted

Enrichment Protocols

1: Enrichment in Primary PSBB, 48 Hrs at 35 C.
2: Enrichment in Primary PSBB, 24 Hrs at 35 C.
1/100 transfer into GN, 24 Hrs at 35 C.

| | 1 | 2 | MICRO | CIN | | McCONKEY | |
|---|---|---|---|---|---|---|---|
| | GT+ | GT+ | Confirm | GN | PSBB | GN | PSBB |
| TOTAL | 23 | 23 | 15 | 5 | 5 | 12 | 6 |

What is claimed is:

1. A nucleic acid probe which hybridizes to the *Yersinia enterocolitica* target nucleic acid 5'-CCAAUAACU-UAAUACGUUGUUGG-3', or the complement of the target nucleic acid, following incubation at 60° C., for 14–16 hours in a hybridization solution containing 0.9M NaCl, 0.12M Tris-HCl, pH 7.8, 6 mM EDTA, 0.1M KPO4, 0.1% SDS, 0.1% pyrophosphate, 0.002% ficoll, 0.02% BSA, and 0.002% polyvinylpyrrolidine, followed by three, 15 minutes post-hybridization washes at 60° C. in a solution containing 0.03M NaCl, 0.004M Tris-HCl, pH 7.8, 0.02 mM EDTA and 0.1% SDS, and which does not hybridize to rRNA or DNA of non-*Yersinia enterocolitica* species selected from the group consisting of *Yersinia kristensenii* (ATCC 55832); *Yersinia kristensenii* (ATCC 55830); *Yersinia fredericksenii* (ATCC 55829); *Yersinia ruckeri* (ATCC 55831); and *Yersinia pseudotuberculosis* (ATCC 55833), under otherwise identical hybridization conditions.

2. A nucleic acid probe of claim 1 comprising contiguous nucleotide residues 5'-CAATCCAACAACGTATTAAGT-TATTGGCCT-3'.

3. A nucleic acid probe of claim 1 comprising contiguous nucleotide residues 5'-CGTCAATCCAACAACGTAT-TAAGTTATTGGCCTTCC-3'.

4. A nucleic acid probe which hybridizes to the *Yersinia enterocolitica* target nucleic acid 5'-CAUAAAGG-UUAAUAACCUUUGUG-3', or the complement of the target, following incubation at 60° C., for 14–16 hours in a hybridization solution containing 0.9M NaCl, 0.12M Tris-HCl, pH 7.8, 6 mM EDTA, 0.1M KPO4, 0.1% SDS, 0.1% pyrophosphate, 0.002% ficoll, 0.02% BSA, and 0.002% polyvinylpyrrolidine, followed by three, 15 minutes post-hybridization washes at 60° C. in a solution containing 0.03M NaCl, 0.004M Tris-HCl, pH 7.8, 0.02 mM EDTA and 0.1% SDS, and which does not hybridize to rRNA or DNA of non-*Yersinia enterocolitica* species selected from the group consisting of *Yersinia kristensenii* (ATCC 55832); *Yersinia kristensenii* (ATCC 55830); *Yersinia fredericksenii*

(ATCC 55829); *Yersinia ruckeri* (ATCC 55831); and *Yersinia pseudotuberculosis* (ATCC 55833), under otherwise identical hybridization conditions.

5. A nucleic acid probe which hybridizes to the *Yersinia intermedia* target nucleic acid 5'-CAGUCGUGUUAAUAGCACGAUUG-3', or the complement of the target nucleic acid, following incubation at 60° C., for 14–16 hours in a hybridization solution containing 0.9M NaCl, 0.12M Tris-HCl, pH 7.8, 6 mM EDTA, 0.1M KPO4, 0.1% SDS, 0.1% pyrophosphate, 0.002% ficoll, 0.02% BSA, and 0.002% polyvinylpyrrolidine, followed by three, 15 minutes post-hybridization washes at 60° C. in a solution containing 0.03M NaCl, 0.004M Tris-HCl, pH 7.8, 0.02 mM EDTA and 0.1% SDS, and which does not hybridize to rRNA or DNA of non-*Yersinia enterocolitica* species selected from the group consisting of *Yersinia kristensenii* (ATCC 55832); *Yersinia kristensenii* (ATCC 55830); *Yersinia fredericksenii* (ATCC 55829); *Yersinia ruckeri* (ATCC 55831); and *Yersinia pseudotuberculosis* (ATCC 55833), under otherwise identical hybridization conditions.

* * * * *